United States Patent
Menon et al.

(10) Patent No.: US 8,610,103 B2
(45) Date of Patent: Dec. 17, 2013

(54) FLEXIBLE MICROCAVITIES THROUGH SPIN COATING

(75) Inventors: Vinod M. Menon, Princeton, NJ (US); Nikesh V. Valappil, Kerala (IN)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 13/144,152

(22) PCT Filed: Jan. 13, 2010

(86) PCT No.: PCT/US2010/020924
§ 371 (c)(1),
(2), (4) Date: Sep. 20, 2011

(87) PCT Pub. No.: WO2010/123592
PCT Pub. Date: Oct. 28, 2010

(65) Prior Publication Data
US 2012/0001149 A1    Jan. 5, 2012

Related U.S. Application Data

(60) Provisional application No. 61/144,610, filed on Jan. 14, 2009, provisional application No. 61/155,406, filed on Feb. 25, 2009.

(51) Int. Cl.
*H01L 29/06* (2006.01)

(52) U.S. Cl.
USPC ...................... 257/9; 257/E33.068

(58) Field of Classification Search
USPC .................. 438/22, 29, 34, 47; 257/9, 98, 99, 257/E33.061, E33.008, E29.071, E51.021, 257/E33.068
See application file for complete search history.

(56) References Cited

U.S. PATENT DOCUMENTS

| | | | |
|---|---|---|---|
| 6,366,017 B1 | 4/2002 | Antoniadis et al. | |
| 6,392,341 B2 * | 5/2002 | Jacobsen et al. | 313/506 |
| 6,436,613 B1 | 8/2002 | Fallahi et al. | |
| 6,627,923 B1 * | 9/2003 | Lipson et al. | 257/102 |
| 2003/0031218 A1 | 2/2003 | Yeh | |
| 2004/0038437 A1 * | 2/2004 | Jaffe et al. | 438/29 |
| 2005/0123974 A1 * | 6/2005 | Gilmanshin et al. | 435/6 |

FOREIGN PATENT DOCUMENTS

WO   WO 2008042337 A2 *   4/2008
WO   WO 2009073002 A1 *   6/2009

* cited by examiner

*Primary Examiner* — Brook Kebede
(74) *Attorney, Agent, or Firm* — Hoffmann & Baron, LLP; Betsy Kingsbury Dowd, Esq.

(57) ABSTRACT

A mechanically flexible array of optically pumped vertical cavity surface emitting lasers, fabricated using spin coating. The array uses InGaP colloidal quantum dots as an active medium and alternating polymer layers of different refractive indices as Bragg mirrors. Enhanced spontaneous emission is produced. The flexible array can be peeled off a substrate, producing a flexible structure that can conform to a wide variety of shapes, and having an emission spectrum that can be mechanically tuned. The flexible array can be used to create a flexible infrared light bandage.

12 Claims, 9 Drawing Sheets

FIG. 8

FLEXIBLE MICROCAVITIES THROUGH SPIN COATING

CROSS REFERENCE TO RELATED APPLICATIONS

This application is a national phase filing under 35 U.S.C. §371 of International application number PCT/US2010/020924, filed Jan. 13, 2010, which claims the benefit of and priority from U.S. Provisional Patent Application Ser. No. 61/144,610, filed Jan. 14, 2009, and U.S. Provisional Patent Application Ser. No. 61/155,406, filed Feb. 25, 2009, both of which are hereby incorporated by reference in their entireties.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of an agreement identified by CUNY Research foundation/campus account number 47156-00 01, Grant no. W911 NF-07-1-0397, awarded by the Army Research Office.

FIELD OF THE INVENTION

One or more embodiments of the present invention relates generally to a method, device, add system related to a mechanically flexible array of microcavity emitters produced using a spin-coating technique.

BACKGROUND OF THE INVENTION

Vertical cavity surface emitting lasers (VCSELs) have found numerous applications ranging from free space, plastic optical fiber, scanning, printing, machine vision, optical switching, displays, multi and single channel communication systems, and short-range fiber optical communication systems using plastic optical fibers (POF). These POFs have a local attenuation minimum at 650 nm and hence VCSELs emitting in this wavelength rage are important for realizing such systems. Most red emitting VCSELs are fabricated using traditional and expensive semiconductor growth techniques such as molecular beam epitaxy and metal organic chemical vapor deposition.

A quantum dot (QD) is a semiconductor whose excitons are confined in all three spatial dimensions. As a result, they have properties that are between those of bulk semiconductors and those of discrete molecules. The conducting characteristics of quantum dots are closely related to the size and shape of the individual crystal making tip the quantum dot. Colloidal quantum dots are synthesized from precursor compounds dissolved in solutions, much like traditional chemical processes. The synthesis of colloidal quantum dots is based on a three-component system composed of: precursors, organic surfactants, and solvents. When heating a reaction medium to a sufficiently high temperature, the precursors chemically transform into monomers. Once the monomers reach a high enough supersaturation level, the nanocrystal growth starts with a nucleation process, eventually producing the quantum dots. An immediate optical feature of colloidal quantum dots is their coloration. While the material which makes up a quantum dot defines its intrinsic energy signature, the nanocrystal's quantum confined size is more significant at energies near the band gap. Thus, because of the quantum confinement effect, quantum dots of the same material, but with different sizes, can emit light of different colors.

Embedding photon emitters such as QDs in microcavities alter their emission properties due to the ability of these structures to confine and enhance electromagnetic fields. Colloidal QDs have been embedded in distributed feedback structures, poly (methylmethacrylate) spheres, silica microspheres, one dimensional microcavities, two and three-dimensional photonic crystals and microdisk structures. Such structures are important for the realization of a compact laser due to their smaller footprint and decreased lasing threshold due to smaller optical mode volumes.

The simplest class of microcavities suitable for lasing is a one dimensional microcavity consisting of a cavity layer sandwiched between two sets of Distributed Bragg Reflectors (DBRs). A DBR is formed from alternating layers of materials with different refractive indices. Each layer has a uniform thickness, and each layer boundary causes a partial reflection of an optical wave. For waves whose wavelength is close to four times the optical thickness of the layers, the many reflections combine with constructive interference, and the layers act as a high-quality reflector. Most DBRs for VCSEL structures are fabricated using techniques such as MBE, MOCVD, plasma enhanced chemical vapor deposition, or sputtering. These methods of manufacturing disadvantageously require expensive manufacturing tools, and are slow to form layers.

In contrast, spin coating is a relatively fast and inexpensive method to spread a material, but conventional spin coating does not provide precise control over the thickness of deposited material. Spin coating has been used where variations in thickness are not critical, such as to form an emissive organic material onto Bragg mirrors and DFB structures. Optically and electrically pumped VCSEL devices have used solid substrates, with the exception of surface emitting lasers utilizing two-dimensional photonic crystal based reflectors with a thick (approximately 1 µm) organic dye based gain medium to realize a flexible laser structure.

Flexible microcavities have been demonstrated using a commercially available reflector film acting as the bottom mirror and a metal mirror as the top mirror. However, the use of metal mirror reduced the reflectivity drastically and hence does not allow the realization of high quality factor microcavities.

Light structures that generate visible radiation have been used to deliver photodynamic therapy. For example a light bandage has been created by combining off the shelf light emitting diodes (LEDs) and embedding them in an epoxy. A disadvantage of such devices is that because they operate in the visible part of the electromagnetic spectrum, they suffer poor effectiveness when used for some applications of the therapy, such as wound healing, which are more effective when used with electromagnetic radiation outside the visible range.

SUMMARY OF THE INVENTION

This invention pertains to the development of a method to produce flexible microcavity structures for realizing novel emitters and display architectures. The microcavity structures are produced by spin coating polymers onto a substrate, such that the microcavity structure can be easily removed from the substrate. The method is adaptable to a wide array of wavelength ranges.

One or more embodiments of the invention provides a method for fabricating a flexible microcavity emitter, the method including spin-coating a first distributed Bragg reflector onto a glassy substrate, spin-coating a polymer layer onto the first distributed Bragg reflector, in which the polymer layer includes a plurality of quantum dots, and spin-coating a second distributed Bragg reflector onto the polymer layer.

Optionally, the method may also include or be further described as spin-coating a layer of a first solvent on top of the glassy substrate, the first solvent including a first polymer dissolved into the first solvent, then repeating, for a first predetermined number of iterations, the steps of: spin-coating a layer of a second solvent on top of the layer of the first solvent, the second solvent including a second polymer dissolved into the second solvent; and spin-coating a layer of the first solvent onto the layer of the second solvent; and then spin-coating a layer of a second solvent on top of the layer of the first solvent, in which the first polymer is substantially insoluble in the second solvent, and the second polymer is substantially insoluble in the first solvent.

Optionally, the first polymer may be polyvinyl carbazole, and/or the second polymer may be cellulose acetate.

Optionally, the method may also include or be further described as: applying the first solvent onto a target, the first solvent including about 28 mg of polyvinyl carbazole dissolved per milliliter of chlorobenzene; spinning the target at a rate of about 3,000 to about 3,150 RPM for about 40 seconds; and heating the target to at least 80° C. for about 15 minutes.

Optionally, the method may also include or be further described as: applying the second solvent onto a target, the second solvent comprising about 30 mg of cellulose acetate dissolved per milliliter of diacetone alcohol; spinning the target at a rate of about 4,500 to about 5,000 RPM for about 40 seconds; and heating the target to at least 120° C. for about 15 in Mutes.

Optionally, the method may also include or be further described as: applying a polymer solution onto the first distributed Bragg reflector, the polymer solution comprising a chlorobenzene solvent having dissolved therein about 39 mg of colloidal solution per milliliter of chlorobenzene, wherein the colloidal solution comprises 30% v/v of quantum dots and the balance polyvinyl carbazole; spinning the first layer of the distributed Bragg reflector a rate of about 2,000 to about 5,000 RPM for about 40 seconds; and heating the layer to at least 95° C. for about 15-20 minutes.

Optionally, the method may also include or be further described as: spin-coating a layer of a second solvent on top of the polymer layer; repeating, for a second predetermined number of iterations, the steps of: spin-coating a layer of a first solvent on top of the layer of the second solvent; and spin-coating a layer of the second solvent onto the layer of the first solvent; and spin-coating a layer of a first solvent on top of the layer of the second solvent.

Optionally, the top DBR may have fewer layers than the bottom DBR.

One or more embodiments of the invention provides a flexible microcavity emitter including a first spin-coated distributed Bragg reflector, a polymer layer spin-coated onto the first distributed Bragg reflector, in which the polymer layer includes a plurality of quantum dots; and a second first spin-coated distributed Bragg reflector, spin-coated onto the polymer layer.

Optionally, the emitter may also include or be further described as being made of a first plurality of polymer periods, the polymer period including a spin-coated layer of a first polymer, and a spin-coated layer of a second polymer, in which the index of refraction of the first polymer differs from the index of refraction of the second polymer by at least a predetermined amount.

Optionally, the emitter may also include or be further described as the first polymer is substantially insoluble in a second solvent, and the second polymer is substantially insoluble in a first solvent.

Optionally, the emitter may also include or be further described as the first polymer including polyvinyl carbazole, and the second polymer including cellulose acetate.

Optionally, the emitter may also include or be further described as the second distributed Bragg reflector including a second plurality of polymer periods, wherein the second plurality is fewer than the first plurality.

One or more embodiments of the invention provides a flexible infrared light bandage, which includes: a first spin-coated distributed Bragg reflector; a polymer layer spin-coated onto the first distributed Bragg reflector, in which the polymer layer includes a plurality of quantum dots, in which the quantum dots are configured to reradiate electromagnetic radiation within a wavelength of about 700 nm to about 1000 nm; a second first spin-coated distributed Bragg reflector, spin-coated onto the polymer layer; and a light source configured to stimulate the quantum dots.

Optionally, the light source used as a pump source to stimulate the quantum dots may be an organic LED. Optionally, the flexible infrared light bandage may also include a portable power source coupled to the light source (e.g., coupled to an organic LED). The portable power source may be a battery or an RFID collector.

BRIEF DESCRIPTION OF THE DRAWINGS

Notwithstanding any other embodiments that may fall within the scope of the present invention, an embodiment of the present invention will now be described, by way of example only, with reference to the accompanying figures, in which.

DETAILED DESCRIPTION

In one or more embodiments of the present invention, there is disclosed a spin coating process to make a flexible microcavity structure using organic materials, and the microcavity structure resulting from the process.

Microcavities that help confine electromagnetic radiation (e.g., light) are useful for realizing highly efficient lasers, single photon emitters and displays. Most microcavity structures known in the prior art are realized using techniques such as molecular beam epitaxy, chemical vapor deposition or sputtering. Compared to these methods, spin coating is a simpler method to deposit material on a substrate. Spin coating is a process that has been used to produce portions of microcavities, but the application of this process to a DBR microcavity structure has been limited due to perceived inability to adequately control the thickness of the deposited materials.

Applicants have discovered and reduced to practice sufficient control over layer thicknesses deposited by spin coating, to enable the spin coating process to be suitable for making a DBR microcavity emitter. Control over layer thickness is accomplished by control of the concentration of dissolved polymer used to make the DBR mirror, and control of spin speed during spin coating. The DBR mirror may also be referred to herein as a DBR reflector. The layer thicknesses were calibrated separately using reflectivity measurements prior the fabrication of the entire structure. Applicants have demonstrated enhanced spontaneous emission (i.e., lasing) from quantum dots embedded in such microcavities fabricated by a spin coating process.

In one or more embodiments of the present invention, Applicants have developed a process whereby successive layers of flexible polymers are spin coated onto a substrate, and quantum dots are included in one or more layers of the flexible polymer, thereby forming a microcavity that can be easily peeled off the substrate. In one or more embodiments of the present invention, Applicants have used the process to produce a solution-processed, mechanically-flexible optically pumped VCSEL emitting at 657 nm. The entire VCSEL structure, including the DBR mirror, is fabricated via spin coating on a glass substrate.

Figure 1:
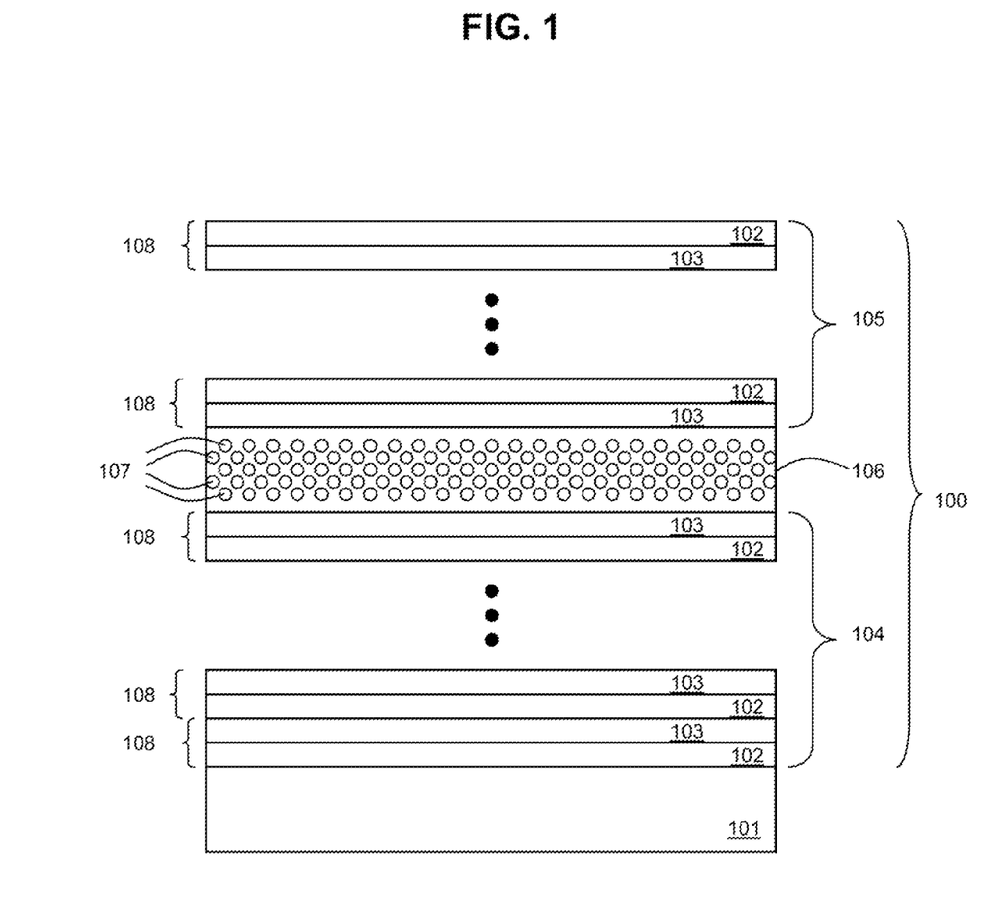
FIG. 1 provides a cross-sectional view of an embodiment of the invention.

A schematic drawing of a microcavity structure fabricated in accord with one or more embodiments of the present invention is shown in FIG. 1. Alternating quarter-wavelength layers of two polymers having different refractive indices are spin coated to fabricate the distributed Bragg reflecting (DBR) mirrors. By arranging the two polymer materials following the quarter wavelength thick rule, the DBR achieves reflectivity over a small wavelength range (i.e., the stop band). The width and reflectivity of the stop band depends on the difference in refractive index of the two layers. A greater difference in the refractive indices of adjacent layers will tend to produce either: greater normalized reflectivity within the stop band for a given number of layers; or will allow usage of fewer layers in order to achieve a desired normalized reflectivity within the stop band. In one or more embodiments, the refractive indexes differ by at least 0.2. The polymers are chosen such that a solvent that dissolves the first polymer does not dissolve the second polymer, and a solvent of the second polymer does not dissolve the first polymer.

In one embodiment, a first polymer layer is made from a material, such as polyvinyl carbazole (PVK), that is soluble in a non-polar solvent; and a second polymer layer is made from a material, such as cellulose acetate (CA) or poly acrylic acid (PAA), that is soluble in a polar solvent. An example of a polar solvent is alcohol, and examples of a non-polar solvent are chlorobenzene and hexane. The refractive indices of PVK and CA are 1.683 and 1.475, respectively, at 650 nm. The polymer layers should also be substantially transparent to light at the operating wavelength of the flexible microcavity structure.

A cavity layer consisting of quantum dots embedded in a flexible plastic material is sandwiched between two DBR mirrors. The flexible plastic material of the cavity layer is selected such that it is soluble in a solvent that is compatible with the carrier solution of the QDs. For example, in one embodiment a nonpolar carrier solution (e.g., toluene or hexane) is used for the QDs, and PVK is used as the flexible plastic material because PVK is soluble in the nonpolar solvent chlorobenzene. In another embodiment, a polar solvent carrier solution (e.g., water) is used for the quantum dots, and CA is used as the flexible plastic material because CA is soluble in the polar solvent alcohol.

The thickness of the cavity layer should be equal to an integer multiple of half the wavelength of emission of the QDs in order to promote lasing. In one embodiment of the invention, a device using InGaP QDs produced an emission wavelength of approximately 670 nm. The microcavity structure included a cavity layer between a top DBR and a bottom DBR having 5 and 10 periods, respectively, in which a period is formed by an adjacent pair of polymer layers. Other numbers of periods can be used for the top and bottom DBRs, based on the desired reflectivity and the quality factor (Q) of the microcavity, Q being a measure of the "goodness" of the cavity and indicates the lifetime of the photon in the cavity. A larger number of layers produces greater reflectivity and hence greater Q. In one embodiment, the top DBR has fewer periods than the bottom DBR, in order to provide better light extraction through the top DBR.

Quantum dots can be based on other material such as cadmium or lead, but commercially available InGaP QDs are a preferable low-toxic alternative due to the absence of heavy metal components.

Fabrication of a VCSEL device in accord with an embodiment of the invention was accomplished by following a procedure which included the following steps:

First, a first Distributed Bragg Reflecting (DBR) mirror was created by spin coating alternating layers of a first polymer and a second polymer onto a substrate such as a glass substrate. This step is explained in greater detail below.

Second, a microcavity structure having embedded quantum dots was spin coated onto the first DBR. This step is explained in greater detail below.

Third, a second DBR mirror was created by spin coating alternating layers of a first polymer and a second polymer were spin coated onto a substrate such as a glass substrate. This step is explained in greater detail below.

In an embodiment, the first polymer selected for the first and second DBR mirror layers was poly-vinyl carbazol (PVK), having an index of refraction of 1.683 at 657 nm. The second polymer selected for the DB layers was cellulose acetate (CA), having an index of refraction of 1.475 at 657 nm. In another embodiment, the first polymer can be CA and the second polymer can be PVK. Different pairs of polymers can also be used for the first and second DBR mirrors. These polymers were selected because: (1) the difference in the index of refraction between adjacent layers provides the individual partially-reflective planes of the first DBR; and the solvent for one polymer does not dissolve the other polymer. For instance, PVK is soluble in non-polar solvents such as chlorobenzene, whereas CA is soluble in polar solvents such as alcohol.

In order to apply each layer of polymer during spin coating of the first and second DBRs, the selected polymers were first dissolved into a solvent. PVK was dissolved into a non-polar solvent (e.g., chlorobenzene) and CA was dissolved into a polar solvent (e.g., diacetone alcohol). Exemplary solvent concentrations were 28 mg/ml of chlorobenzene, and 30 mg/ml of diacetone alcohol.

The first layer of the first DBR was spin-coated onto a substrate. Spin-coating generally involves dropping a solution onto a substrate, such that a substantial area to be coated is covered, and then the target is spun with an acceleration period (e.g., 10 sec), followed by a constant spin period at the desired RPM (e.g., 30 sec), and finally decelerating to a stop. Other acceleration profiles are usable by persons of skill in the art. A glass, glass-like, or ceramic substrate is preferred because the adhesion of the DBR to the substrate is less than the tensile strength of the complete fabricated VCSEL device, thereby allowing the complete fabricated VCSEL device to be removed from the substrate by peeling. The substrate may also be flexible and attached to a rigid base, as long as the adhesion of the microcavity to the substrate is low enough to permit the microcavity to be peeled. In one embodiment, the first layer deposited onto the substrate is PVK, and in another embodiment the first layer is CA. For simplicity of discussion below, it will be assumed that the first layer is PVK unless expressly indicated otherwise. For further simplicity below, it should be understood that "glass substrate" also refers to glass-like or ceramic substrates unless the context clearly indicates otherwise.

The substrate is spinning as each layer of the first DBR is being dripped onto the substrate. The rate of spin and duration of spin are determined by the viscosity of the uncured dissolved polymer and the desired thickness of the resulting layer. Viscosity is controlled by the concentration of the dissolved polymer solutions. Each cured layer of PVK and CA is designed to have a thickness of $\lambda/4n$, where n is the index of refraction for the polymer of the layer and $\lambda$ is the free-space wavelength of the quantum dot emission used in the cavity. The curing process introduces a small amount of shrinkage of the polymer layers, so the uncured polymers should be deposited approximately 10 nm thicker than the intended cured thickness.

For instance, the PVK layers are spun at about 3,000-3,150 RPM for approximately 40 seconds and then placed on a hotplate at 80° C. curing temperature for approximately 15 minutes curing time to remove the solvent, resulting in PVK layer thicknesses of approximately 90 nm. The CA layers are spun at about 4,500-5,000 RPM for approximately 40 seconds, and placed on a hotplate at 120° C. curing temperature for approximately 15 minutes curing time to remove the solvent, resulting in CA layer thicknesses of approximately 100 nm. The curing temperature should be chosen to be at least as high as the evaporation temperature of the solvent in the layer to be cured. Higher curing temperatures will generally result in shorter curing times.

One set of alternating polymer layers so constructed constitutes a period. This process is repeated for the desired number of periods. The resulting DBR mirror has been shown to have excellent uniformity in its reflectivity over a 2 cm×2 cm sample, as will be explained in further detail below in relation to FIG. 4.

Next, the microcavity structure having embedded quantum dots was spin coated onto the first DBR. Quantum dots having an InGaP core and ZnS shell, and having peak emission wavelength of 650 nm and nanocrystal diameter of approximately 6 nm were used because such QDs provide sufficient optical output when stimulated in order to produce lasing at 657 nm. InGaP QDs were used here because they do not have any high toxicity elements such as cadmium or lead, unlike QDs made from CdSe, PbS, or PbSe. The QDs were dispersed into a carrier solution of toluene at a concentration of approximately 2.0 mg/ml. Quantum dots having these characteristics are commercially available from Evident Technologies. Other carriers such as chlorobenzene, hexane, or an aqueous solution besides toluene can be used The QDs in carrier solution were then dispersed into a PVK solution. The concentration of QDs in PVK was optimized to obtain the maximum emission intensity, which was found to be 30% v/v of colloidal QDs with respect to the PVK solution (39 mg/ml) by dispersing 0.3 ml of the QDs in 1 ml of PVK solution. This corresponds to a fill factor of approximately 2% of QDs in the cavity layer.

A PVK cavity layer having a thickness of $\lambda/2n_{pvk}$ (i.e., approximately 190 nm) with the embedded QDs is then spin coated at approximately about 2,000 to about 5,000 RPM for about 40 seconds; and heating the layer to at least 95° C. for about 15-20 minutes. The curing time and temperature depends upon the thickness of the layer to be produced. Here, $n_{pvk}$ is the refractive index of the PVK.

Next, the second DBR is formed above the microcavity structure. The first layer of the second DBR, i.e., the layer in contact with the microcavity structure, is a different polymer than the polymer of the microcavity structure. For instance, if the microcavity structure is made from PVK, the first layer of the second DBR is made from CA. The second DBR is constructed from alternating layers of the first polymer and the second polymer, in the same spin-coated fashion as the first DBR. Typically, the second DBR will be constructed with fewer layers than the first DBR, in order to promote emission of light through the second DBR. For instance, if the first DBR is formed with 10 layers, the second DBR may be formed with 5 layers.

Following the fabrication of the second DBR, the microcavity structure can be peeled off the glass substrate to form a flexible free standing microcavity.

Turning now to FIG. 1 there is illustrated a cross-sectional view of a microcavity structure 100 constructed atop substrate 101 in accord with an embodiment of the invention. First atop substrate 101, which is made from glass or a glass-like material such as a ceramic, there is formed a first DBR 104. First DBR 104 is made from alternating layers 102 of a first polymer and layers 103 of a second polymer. The polymers making up layers 102, 103 are selected as described above, and layers 102, 103 are formed by the spin coating process described earlier. An alternating pair of adjacent layers 102, 103 form a period 108. The number of periods 108 forming first DBR 104 is predetermined by the desired optical characteristics of the microcavity structure. More periods 108 in the first DBR will reduce the FWHM spectral width of the light emitted from microcavity structure 100. In one embodiment, the first polymer is PVK and the second polymer is CA. In another embodiment, the first polymer is CA and the second polymer is PVK.

Atop first DBR 104 there is formed a cavity layer 106, having embedded therein a plurality of quantum dots 107. Quantum dots 107 are substantially uniformly distributed throughout cavity layer 106, and may have any arrangement within cavity layer 106, such as a lattice arrangement or an amorphous arrangement. Cavity layer 106 is based upon the same plastic material as layer 102, i.e., the first polymer, but may have a different thickness and be made from a different concentration of dissolved polymer than layer 102, as described above.

Atop cavity layer 106 there is formed a second DBR 105. Second DBR 105, like first DBR 104, is made from alternating layers 102 of a first polymer and layers 103 of a second polymer. The first layer of second DBR 105 (i.e., the layer in contact with cavity layer 106) is made from the second polymer. Preferably, second DBR 105 includes fewer periods 108 than the number of periods 108 in first DBR 104. In one exemplary embodiment, first DBR 104 can be made from ten periods 108, and second DBR 105 can be made from five periods 108.

Figure 2A:
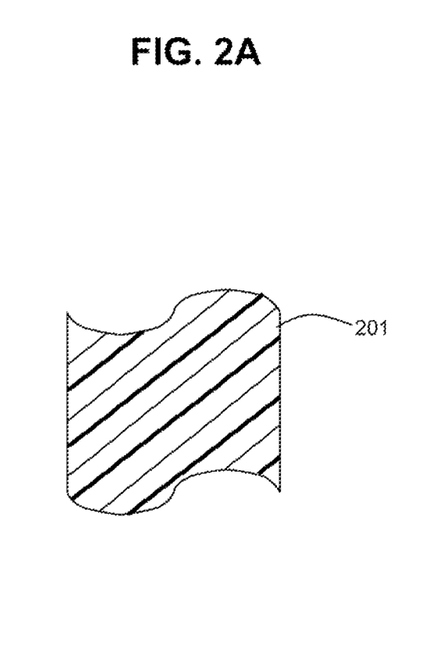
FIG. 2A provides a top elevational view of a free-standing device according to an embodiment of the invention.
Figure 2B:
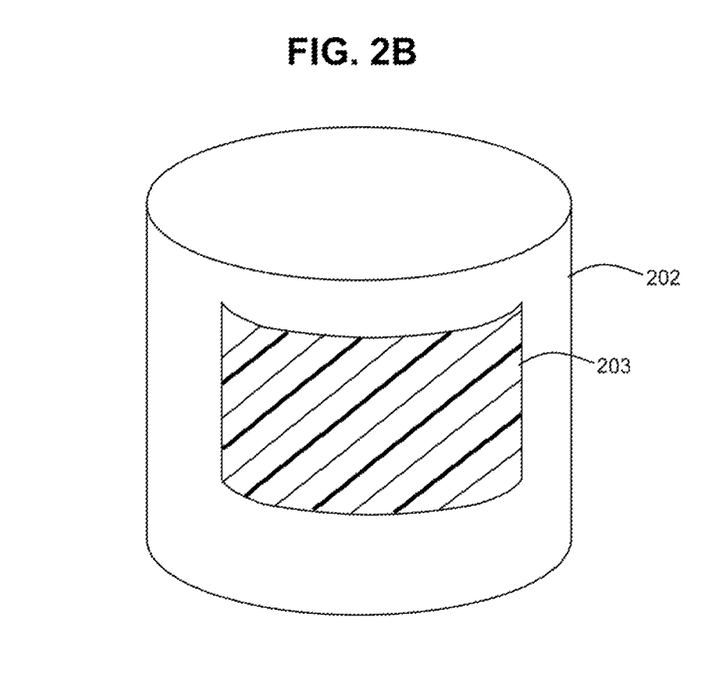
FIG. 2B provides a front and top perspective view of a device according to an embodiment of the invention, adhering to the side surface of a cylinder.

Microcavity structure 100 is peelable from substrate 101, thereby forming a flexible, free-standing microcavity structure. Referring now to FIG. 2A, there is illustrated a perspective view of an exemplary flexible, free-standing microcavity structure 201 after being peeled from substrate 101. Referring now to FIG. 2B, there is illustrated a perspective view of an exemplary flexible, microcavity structure 203 affixed to an object 202, such as a side surface of a cylinder. The microcavity structure 203 can be affixed by any method or device, such as static attraction, suction, and/or adhesive. The microcavity structure 203 so affixed is energized by illumination of the quantum dots 107 by light within a wavelength range that the quantum dots 107 are responsive to. It can be seen from FIG. 2B that microcavity structure 203 substantially conforms to the shape of object 202, and more generally that microcavity structure 203 can conform to substantially any shape.

Figure 3:
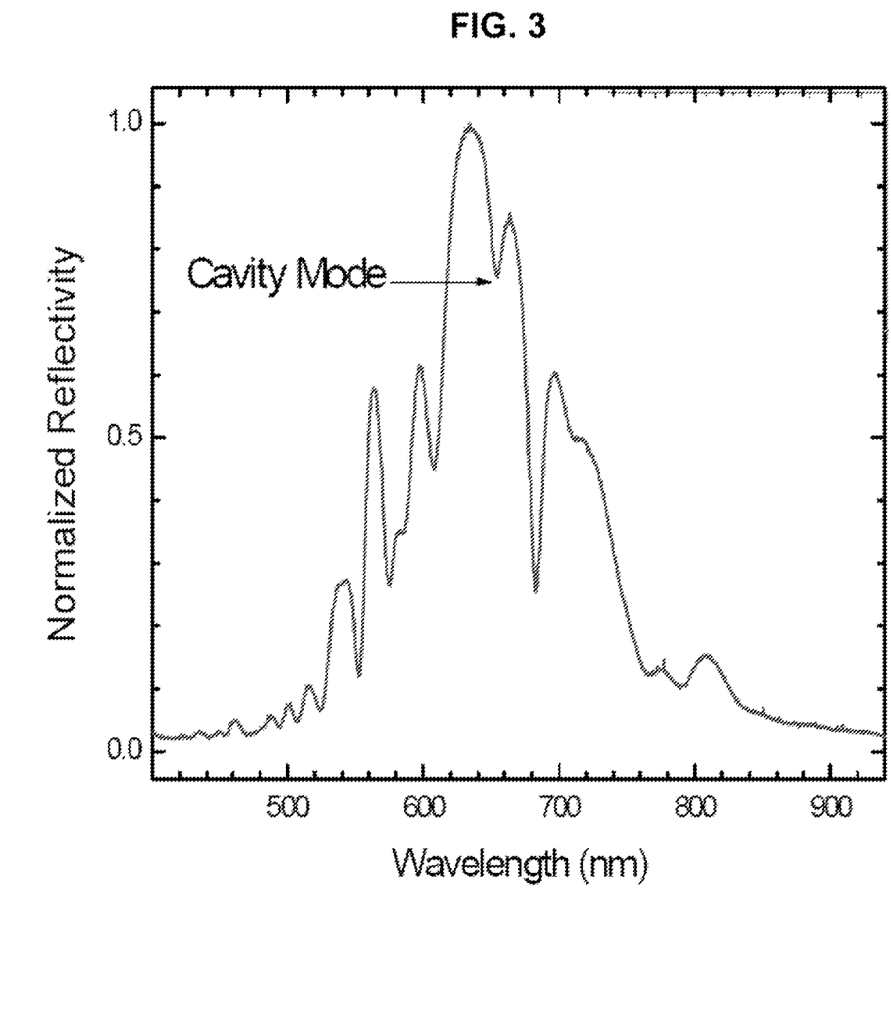
FIG. 3 provides a plot of reflectivity at normal incidence of an embodiment of the invention.
Figure 4:
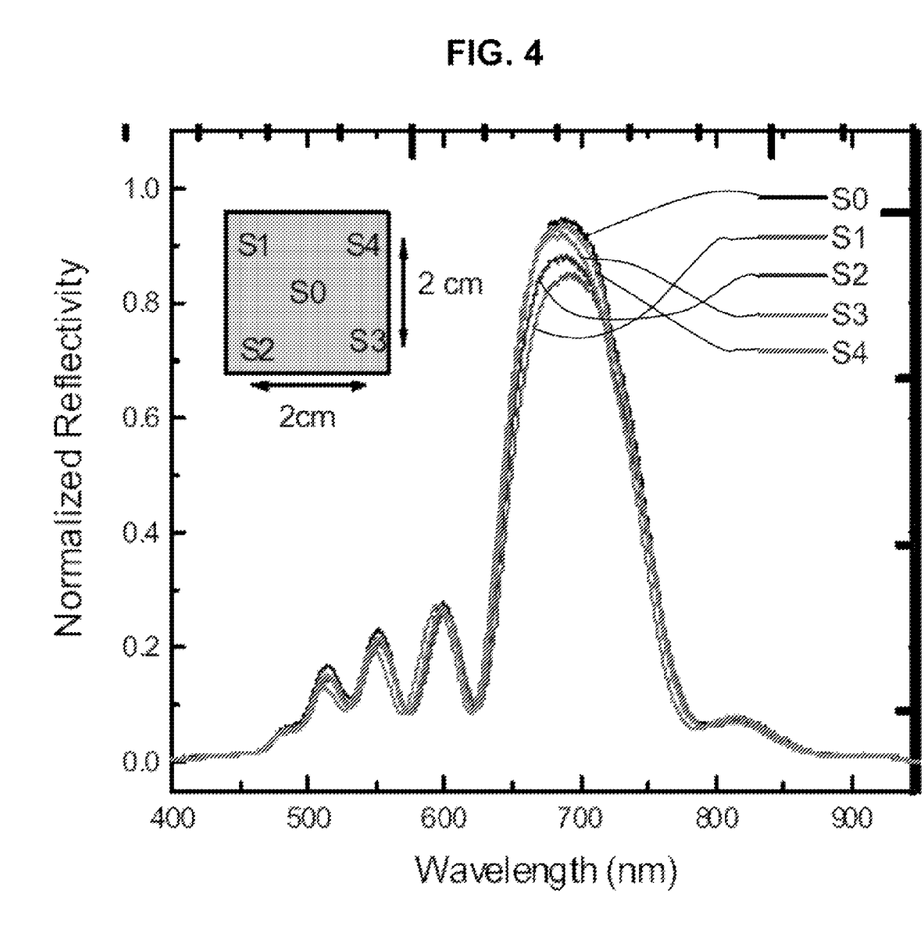
FIG. 4 provides a plot of reflectivity of a distributed Bragg reflector in accord with an embodiment of the invention.

An optical microcavity 100 of approximately 2 cm square was fabricated using a first DBR 104 having 20 periods, and a second DBR 105 having 10 periods. The fabricated optical microcavity 100 was tested using reflectivity and photoluminescence (PL) measurements. All optical measurements reported here were carried out at room temperature. Steady state PL measurements were carried out using the 488 nm line of an argon-ion laser as the excitation source. Reflectivity measurements were carried out using a fiber coupled Tungsten-Halogen lamp as the white light excitation source. FIG. 3 shows the experimental reflectivity of the microcavity structure at normal incidence. FIG. 4 shows the experimental reflectivity of the bottom Bragg mirror having 20 periods, measured at five different locations S0, S1, S2, S3 and S4 on the sample. The inset of FIG. 4 illustrates the location on the microcavity 100 of each of measurement locations S0-S4. The measurements of FIG. 4 indicate over 95% reflectivity and good uniformity, as indicated by the high amount of overlap of curves S0-S4. Light from the excitation source was focused to spot size of approximately 0.5 mm in diameter and the reflected light was collected by a fiber coupled spectrometer. The spectral position of the cavity mode was designed to overlap with the emission maximum of the InGaP/ZnS core/shell QDs. The quality factor of the microcavity was found to be approximately 70.

Figure 5:
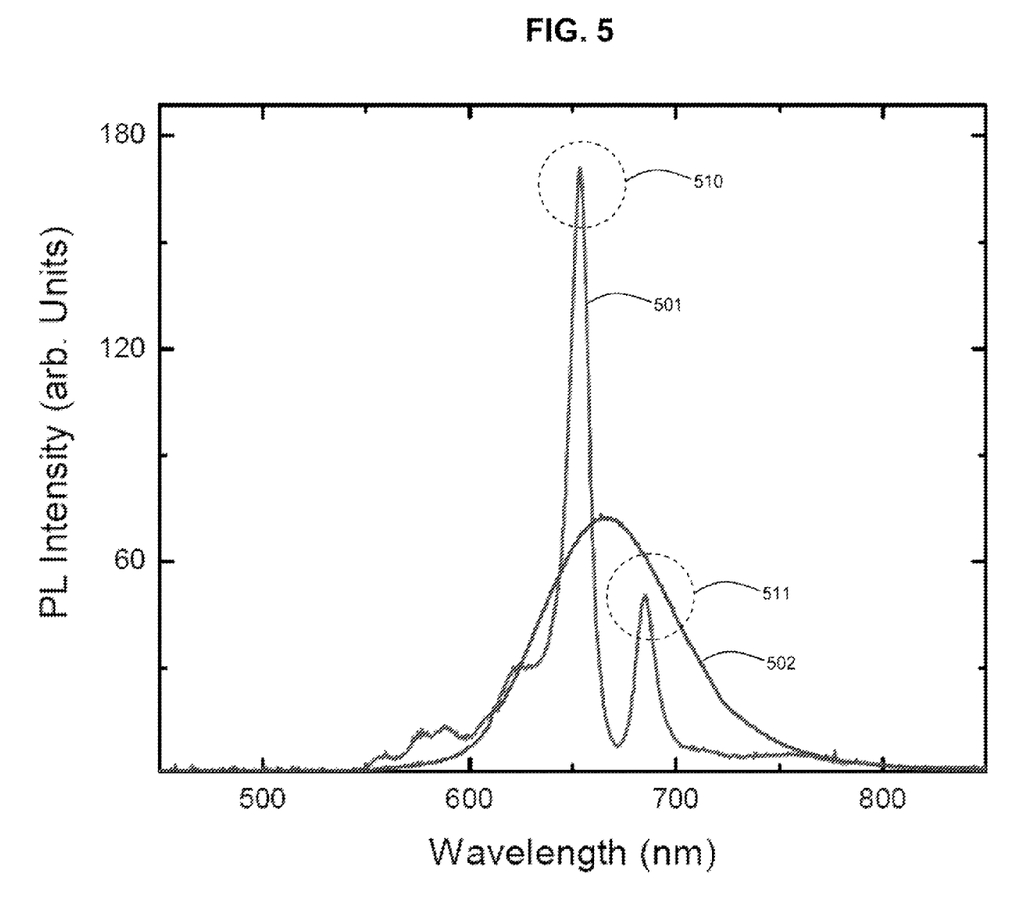
FIG. 5 provides a plot of steady state photoluminescence spectrum of InGaP quantum dots in a microcavity and in toluene.

Referring to FIG. 5, there is shown a first plot 501 of PL intensity as a function of wavelength, for QDs in the tested microcavity. Luminescence maximum 510 corresponds to the cavity mode, and luminescence maximum 511 corresponds to the band edge modes. For comparison, second plot 502 illustrates PL as a function of wavelength for bare QDs in toluene, i.e., not in a microcavity. First plot 501 showed that the cavity linewidth limited narrower emission, with the integrated spectral intensity being approximately two times that of second plot 502, i.e., QDs not in a microcavity.

Figure 6A:
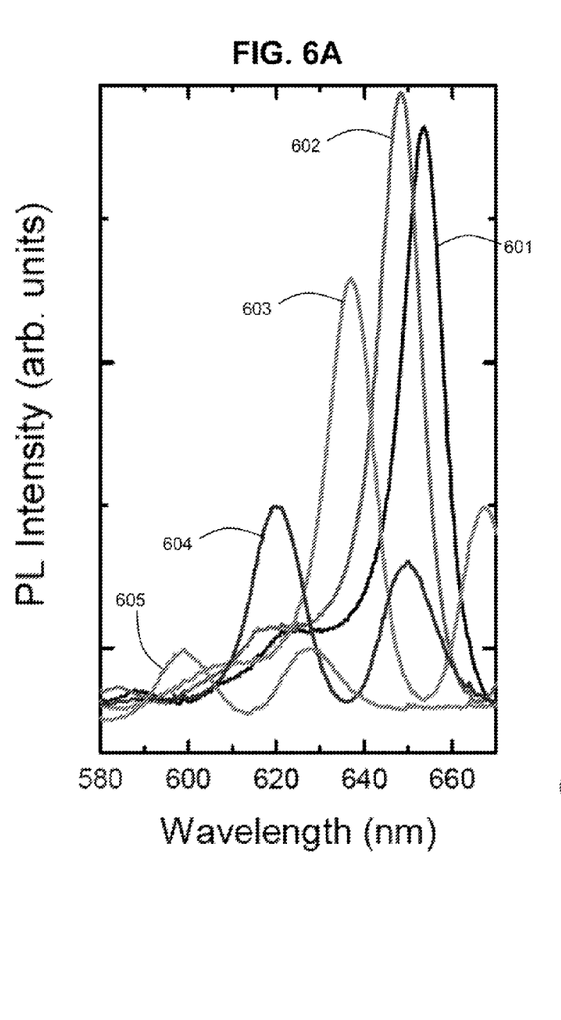
FIG. 6A provides an illustration of angle dependency of the photoluminescence spectrum of an embodiment of the invention on a flat surface.

Results of angle resolved PL measurements are shown in FIG. 6A. Curve 601 is measured along the axis of emission of the microcavity, i.e., 0° off axis. Curves 602, 603, 604, and 605 are measured at 10°, 20°, 30°, and 40° off axis, respectively. The emission spectrum follows the cavity mode until approximately 40° off axis. Beyond this point, the emission maximum of the QDs lies outside the stop band of the DBR and hence does not show any angle dependence. The above measurements were carried out with the tested microcavity laid out on a flat substrate. Following this, the tested microcavity was wrapped around glass cylinders with different radii.

Figure 6B:
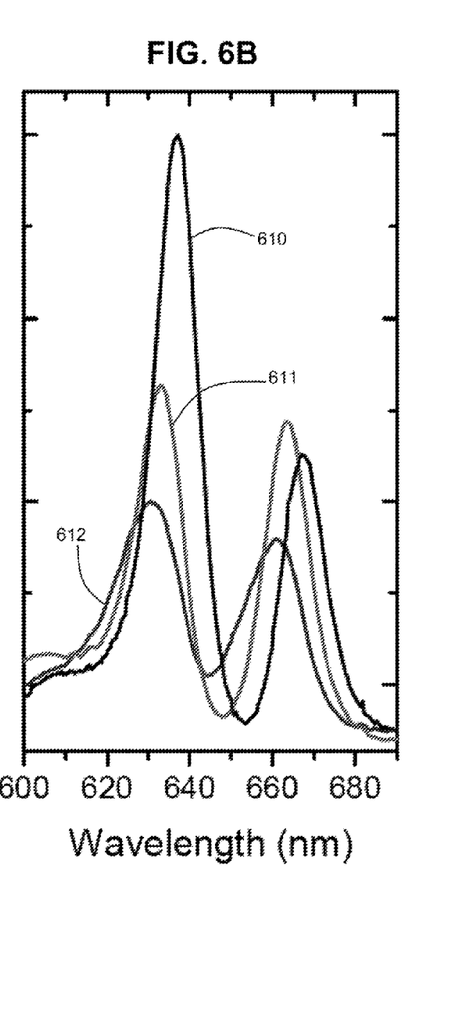
FIG. 6B provides an illustration of wavelength and amplitude shift as a function of bend radius.

The PL emission collected at 20° was compared for the three cases and is shown in FIG. 6B. Curve 610 is the emission spectrum with the microcavity laid flat. Curves 611 and 612 are the emission spectrums with the microcavity bent to a radius of 1.0 and 0.5 cm, respectively. Upon bending the tested microcavity to smaller radii, the emission wavelength shifts in the blue direction and the intensity of emission decreases. This effect was observed only for non-normal collection angles since light being emitted normal originates from the cavity region that is not curved by the bending.

Figure 7:
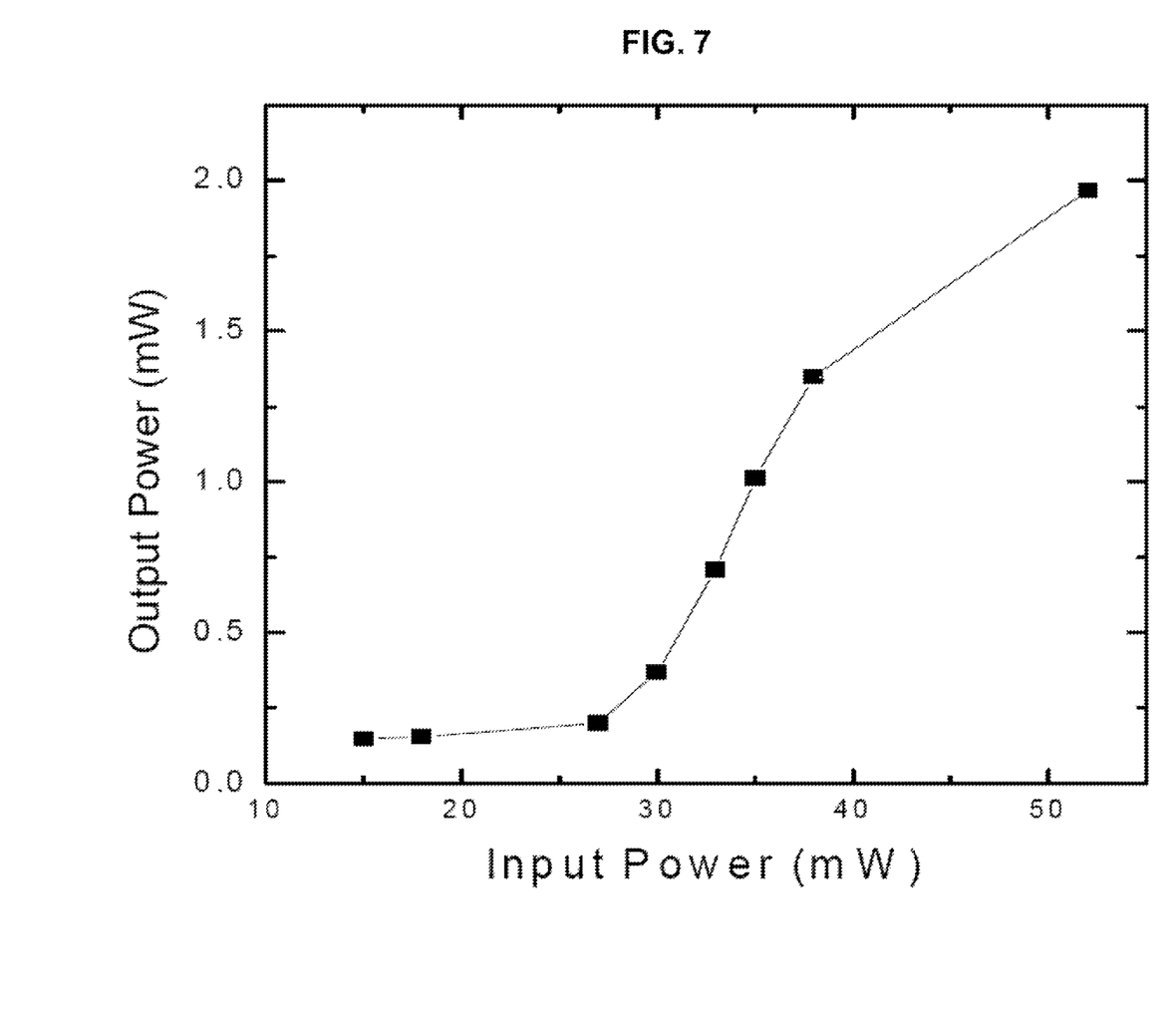
FIG. 7 provides a plot of output power as a function of input power for an embodiment of the invention.
Figure 8:
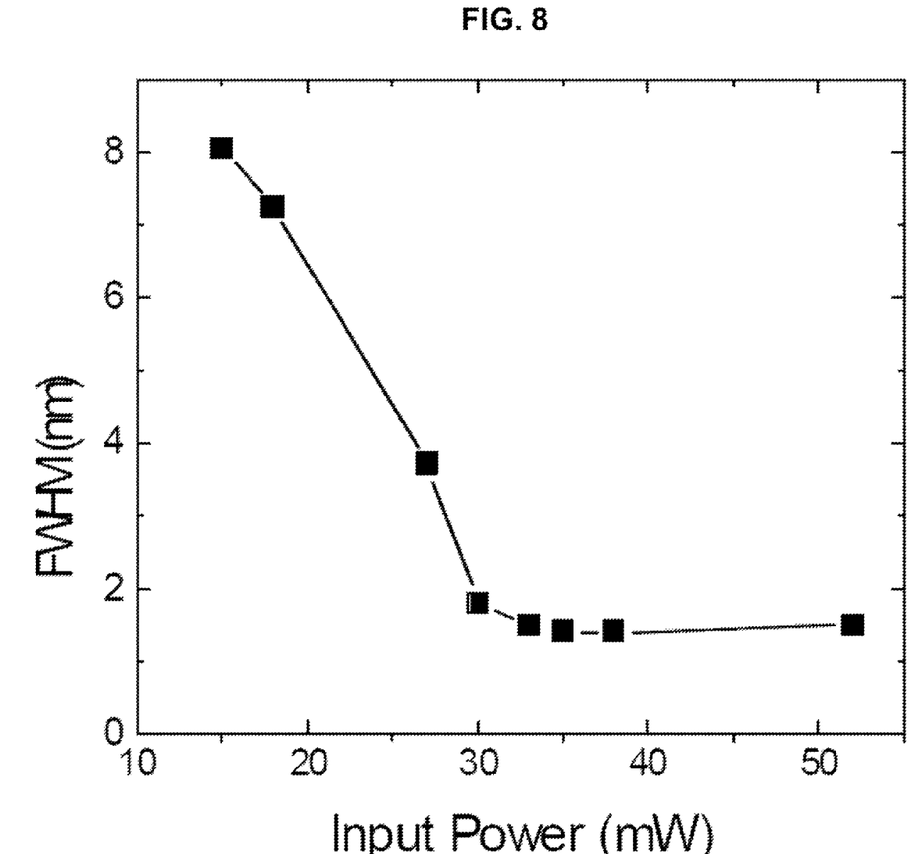
FIG. 8 provides a plot of full-width, half-maximum bandwidth as a function of input power.
Figure 9:
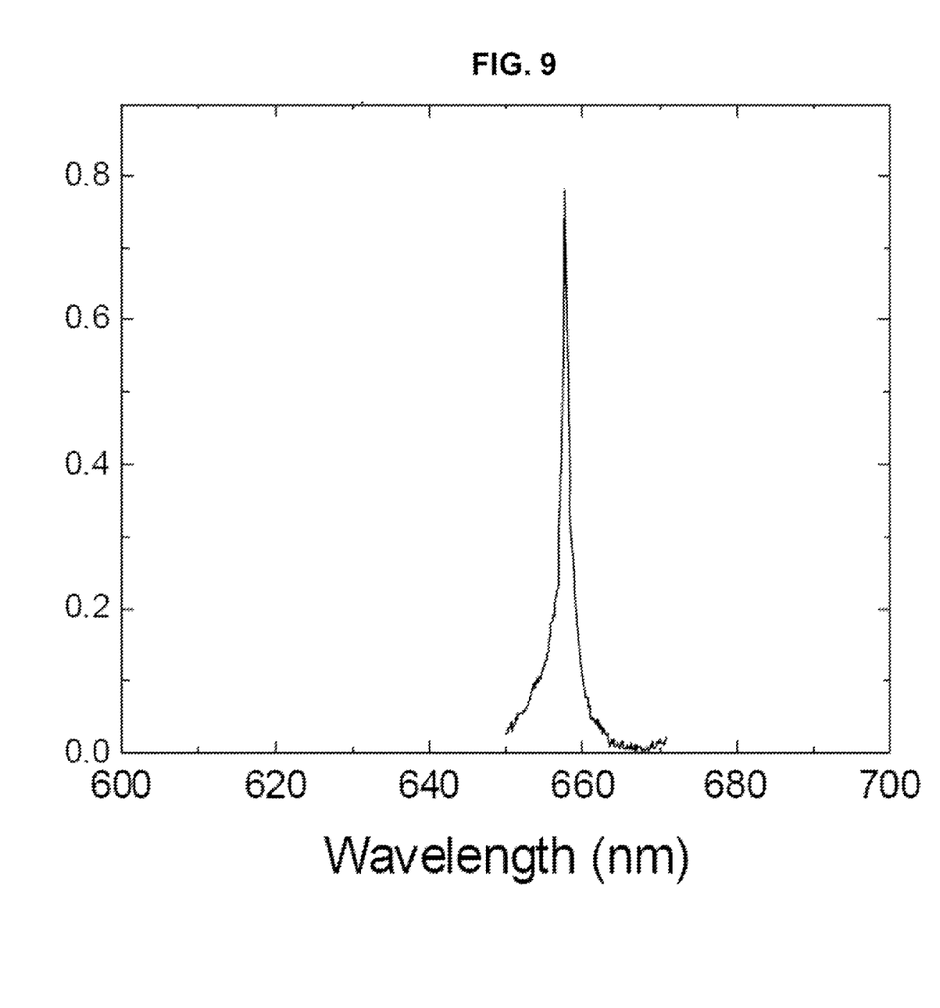
FIG. 9 provides a normalized spectral plot of an embodiment of the invention at lasing.

To characterize the lasing properties of the flexible microcavity structure, the device was optically pumped using the second harmonic of an NdYAG laser (532 nm) with 5 ns pulses operating at 10 Hz. The emission from the device was collected using a fiber coupled spectrometer. The input pump power was varied using a variable attenuator. FIG. 7 shows the average output power as a function of average pump power. As can be seen from FIG. 7, the lasing threshold is at 27 mW and the slope efficiency (at the highest output power) is approximately 12%. At pump power greater than 50 mW, the laser output was found to saturate primarily due to heating effects. FIG. 8 plots the variation of the full width at half maximum (FWHM) at the lasing wavelength as a function of pump power. The FWHM shows a threshold behavior consistent with the light output versus input measurements. FIG. 9 illustrates the emission spectra obtained above the lasing threshold. The observation of threshold in light output as well as significant linewidth narrowing above threshold provides clear evidence of lasing in the flexible microcavity discussed here.

By appropriate selection of microcavity structure sizes and QD emission characteristics, it is possible to produce a microcavity emitter which generates lasing light having a fixed wavelength within the range of at least approximately 300 nm to 1600 nm, thereby producing an electromagnetic source usable for applications spanning ultraviolet, visible, infrared, and telecommunication wavelengths.

A usage of a flexible microcavity emitting infrared electromagnetic energy (i.e., infrared light) is for ambulatory photodynamic therapy. It has been shown that infrared light can be used for healing wounds. This is because infrared light expands veins exposed to the therapy, which in turn lead to greater blood flow in the regions near the wounds, thereby helping the healing process. Furthermore, the cells exposed to the therapy also react favorably to IR light. Photobiomodulation by light in the red to near infrared range (630-1000 nm) has been shown to accelerate wound healing, improve recovery from ischemic injury in the heart and attenuate degeneration in the injured optic nerve. The therapeutic effects of red to near infrared light may result, in part, from intracellular signaling mechanisms triggered by the interaction of near infrared light with the mitochondrial photoacceptor molecule cytochrome c oxidase.

A light bandage has been demonstrated that was assembled from off-the-shelf LEDs, and with the LEDs being embedded in an epoxy. However, a disadvantage of this demonstrated product is that it operates in the visible part of the electromagnetic and hence can not be applied to the present application for wound healing using infrared energy.

In a further embodiment of the invention, a light emitting bandage useful for photodynamic therapy in a wound healing application is described, based on usage of flexible microcavity light emitters, including lasers made from such flexible microcavity light emitters. Advantages of such light emitting bandages are that they can be compact, can be placed in locations that would be inconvenient to illuminate with a conventional IR source (e.g., in a body cavity), can emit more targeted IR energy than conventional IR sources, and can more efficiently provide IR energy than an IR source external to a conventional bandage. In the wound healing application, infrared emitting quantum dots will be used. The infrared QDs may be made, for example, from indium phosphide, lead sulphide, or selenide.

Following fabrication of a microcavity for infrared emission, using the process described earlier, the optical characteristics were tested while the microcavity was still on the glass substrate. The device demonstrated excellent uniformity in its optical properties over a 1 inch×1 inch sample. The emission from the QDs embedded in the microcavity structure showed enhanced spontaneous emission evidenced by the significant reduction in the spectral width and increased intensity in comparison to the bare QDs. The emission from the microcavity also showed angle dependence as expected from any microcavity on a flat surface. Following the optical characterization of the microcavity of the glass substrate, the microcavity structure was demonstrated peelable off the substrate. The microcavity is optically pumped by an optical pump source that produces a higher energy (i.e., shorter wavelength), such as an LED, or other light source, which in turn is connected to a portable power source. The pump source generally cannot produce sufficient directed infrared energy to be used directly as a light bandage. The optical pump source may be, for instance, a commercial LED, laser, or organic LED (OLED). The portable power source may be, for instance, a battery or an RFID collector.

An OLED is a light-emitting diode whose emissive electroluminescent layer is composed of a film of organic compounds. The layer usually contains a polymer substance that allows suitable organic compounds to be deposited. They are deposited in rows and columns onto a flat carrier by a simple "printing" process. The resulting matrix of pixels can emit light of different colors. Usage of an OLED as an optical pump for a light emitting bandage helps allow the light emitting bandage to be thin and flexible. The light produced by the OLED can also be used to stimulate the quantum dots more uniformly than other types of more discrete light sources.

Those skilled in the art will appreciate that the invention described herein is susceptible to variations and modifications other than those specifically described. It should be understood that the invention includes all such variations and modifications which fall within the spirit and scope of the invention.

The invention claimed is:

1. A flexible infrared light bandage comprising: a first spin-coated distributed Bragg reflector; a polymer layer spin-coated onto the first distributed Bragg reflector, the polymer layer including a plurality of quantum dots, wherein the quantum dots are configured to reradiate electromagnetic radiation in the red to near infrared range; a second first spin-coated distributed Bragg reflector, spin-coated onto the polymer layer; and a light source configured to stimulate the quantum dots.

2. The flexible infrared light bandage of claim 1, wherein the first distributed Bragg reflector comprises a first plurality of polymer periods, said polymer period comprising: a spin-coated layer of a first polymer; and a spin-coated layer of a second polymer, wherein: the index of refraction of the first polymer differs from the index of refraction of the second polymer by at least a predetermined amount.

3. The flexible infrared light bandage of claim 1, wherein the first polymer is substantially insoluble in a second solvent, and the second polymer is substantially insoluble in a first solvent.

4. The flexible infrared light bandage of claim 1, wherein the first polymer comprises polyvinyl carbazole, and the second polymer comprises cellulose acetate.

5. The flexible infrared light bandage of claim 1, wherein the second distributed Bragg reflector comprises a second plurality of polymer periods, wherein the second plurality is fewer than the first plurality.

6. The flexible infrared light bandage of claim 1, further comprising a portable power source coupled to the light source.

7. The flexible infrared light bandage of claim 6, wherein the light source is an organic LED.

8. The flexible infrared light bandage of claim 6, wherein the portable power source comprises one of a battery and an RFID collector.

9. The flexible infrared light bandage of claim 1, wherein the reradiated electromagnetic radiation is in the infrared range.

10. The flexible infrared light bandage of claim 9, wherein the reradiated electromagnetic radiation has a wavelength of from about 700 to 1000 nanometers.

11. The flexible infrared light bandage of claim 1, wherein the reradiated electromagnetic radiation has a wavelength of from 630 to 1000 nanometers.

12. The flexible infrared light bandage of claim 1, wherein the quantum dots are selected from the group consisting of indium phosphide, lead sulphide and selenide.

* * * * *